(12) United States Patent
Lee et al.

(10) Patent No.: US 12,178,755 B2
(45) Date of Patent: Dec. 31, 2024

(54) INTRAOCULAR MICRO-DISPLAY SYSTEM WITH INTELLIGENT WIRELESS POWER DELIVERY

(71) Applicant: Verily Life Science LLC, Dallas, TX (US)

(72) Inventors: Shungneng Lee, Sunnyvale, CA (US); Dimitri Azar, Chicago, IL (US)

(73) Assignee: Verily Life Sciences LLC, Dallas, TX (US)

( * ) Notice: Subject to any disclaimer, the term of this patent is extended or adjusted under 35 U.S.C. 154(b) by 438 days.

(21) Appl. No.: 17/609,754

(22) PCT Filed: Mar. 23, 2020

(86) PCT No.: PCT/US2020/024209
§ 371 (c)(1),
(2) Date: Nov. 8, 2021

(87) PCT Pub. No.: WO2020/231519
PCT Pub. Date: Nov. 19, 2020

(65) Prior Publication Data
US 2022/0226156 A1    Jul. 21, 2022

Related U.S. Application Data

(60) Provisional application No. 62/846,428, filed on May 10, 2019.

(51) Int. Cl.
*A61F 9/08*  (2006.01)
*A61F 2/14*  (2006.01)
(Continued)

(52) U.S. Cl.
CPC ............... *A61F 9/08* (2013.01); *A61F 2/14* (2013.01); *A61F 2250/0002* (2013.01); *H04N 7/0127* (2013.01); *H04N 7/183* (2013.01)

(58) Field of Classification Search
CPC ...... A61F 2/14; A61F 9/08; A61F 2250/0001; A61F 2250/0002; H04N 7/183
See application file for complete search history.

(56) References Cited

U.S. PATENT DOCUMENTS 7,012,588 B2   3/2006  Siwinski
7,496,174 B2   2/2009  Gertner et al.
(Continued)

FOREIGN PATENT DOCUMENTS

EP   1585462   2/2017
EP   1996968   3/2017
(Continued)

OTHER PUBLICATIONS

International Search Report and Written Opinion for International Application No. PCT/US2020/024209 mailed Aug. 27, 2020, 13 pages.
(Continued)

*Primary Examiner* — Javier G Blanco
(74) *Attorney, Agent, or Firm* — Haynes and Boone, LLP

(57) ABSTRACT

An intraocular micro-display system includes an intraocular micro-display (IOMD) implant and an auxiliary head unit for delivering power and image data to the IOMD implant. The IOMD implant includes an enclosure shaped for implantation into an eye, a micro-display to emit images towards a retina, an energy storage unit to power the micro-display, a charging antenna for wireless charging of the energy storage unit via a power signal incident upon the first charging antenna, and a data antenna to wirelessly receive the image data for driving the micro-display to emit the images. The charging antenna and the data antenna are implantable into the eye with the IOMD implant.

20 Claims, 7 Drawing Sheets

(51) Int. Cl.
*H04N 7/01* (2006.01)
*H04N 7/18* (2006.01)

(56) References Cited

U.S. PATENT DOCUMENTS

| | | | |
|---|---|---|---|
| 8,179,391 B2 | 5/2012 | Hong et al. | |
| 9,042,028 B2 | 5/2015 | Choi et al. | |
| 9,791,700 B2 | 10/2017 | Schowengerdt | |
| 9,997,585 B2 | 6/2018 | Kasai | |
| 10,251,780 B2 | 4/2019 | Tai et al. | |
| 2004/0117011 A1 | 6/2004 | Aharoni et al. | |
| 2011/0205259 A1 | 8/2011 | Hagood, IV | |
| 2015/0182330 A1* | 7/2015 | Grant | A61F 2/1624 623/6.37 |
| 2016/0058324 A1 | 3/2016 | Cao | |
| 2017/0075414 A1 | 3/2017 | Grant et al. | |
| 2018/0071146 A1 | 3/2018 | Liran et al. | |
| 2019/0012989 A1 | 1/2019 | Deering et al. | |

FOREIGN PATENT DOCUMENTS

| | | | | |
|---|---|---|---|---|
| KR | 20160112536 A | * | 9/2016 | ............... A61F 9/08 |
| WO | 2006015315 | | 2/2006 | |
| WO | 2008153592 | | 12/2008 | |
| WO | 2007006376 | | 1/2017 | |

OTHER PUBLICATIONS

"Argus II: the life-changing retinitis pigmentosa treatment," SecondSight, retrieved from the Internet <https://www.secondsight.com/discover-argus/>, May 20, 2019, 8 pages.

Shim, BS, Sarah Y., et al., "Feasability of Intraocular Projection for Treatment of Intractable Corneal Opacity," Corenea, vol. 38, No. 4, Apr. 2019, pp. 523-527.

Wu, Jiande, et al., "Wireless Power and Data Transfer via a Common Inductive Link Using Frequency Division Multiplexing," IEEE Transactions on Industrial Electronics, Jul. 9, 2015, 10 pages.

* cited by examiner

INTRAOCULAR MICRO-DISPLAY SYSTEM WITH INTELLIGENT WIRELESS POWER DELIVERY

CROSS-REFERENCE TO RELATED APPLICATIONS

This application claims the benefit of U.S. Provisional Application No. 62/846,428, filed May 10, 2019, which is hereby incorporated by reference in its entirety.

TECHNICAL FIELD

This disclosure relates generally to ophthalmic devices, and in particular but not exclusively, relates to intraocular micro-displays.

BACKGROUND INFORMATION

Disease or injury to the cornea can lead to opacification or significant optical damage to the cornea, such that the individual is effectively rendered blind. The blindness may occur despite the patient having a fully functioning retina. For these patients with an intact retina but otherwise blind due to vascularization or damage to the cornea, implantation of an intraocular micro-display in the excised lens of the eye (e.g., capsular sack region) can restore image reproduction onto their fully functioning retina, thereby returning vision to the patient.

A proposed solution for an electronic intraocular micro-display involves the use of a transcutaneous tether that couples a wireless transmitter positioned behind the ear to the intraocular micro-display. This tether provides power and data communication to the intraocular micro-display. The transcutaneous nature and complex surgery required for this proposed solution, likely makes this solution prone to physiological compatibility issues and inflammation. Since the tether protrudes outside of the eye and back into subcutaneous flesh on the side of the face, the tether also presents an infection risk.

To avoid the use of a transcutaneous tether, the intraocular micro-display and related circuitry must have a sufficiently compact form factor to fit entirely within the eye in the region of the capsular sack. As such, power delivery, power storage, and power management of such a small display system presents a significant challenge.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
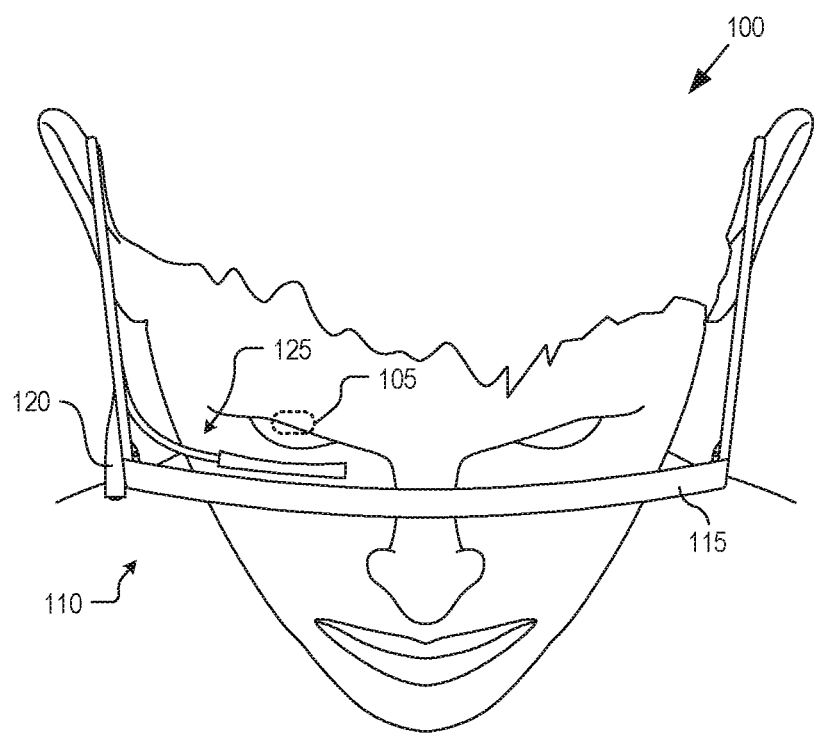
FIGS. 1A and 1B are plan and side view illustrations of an intraocular micro-display (IOMD) system including an IOMD implant and an auxiliary head unit, in accordance with an embodiment of the disclosure.

Embodiments of a system, apparatus, and method of operation for delivering power and image data to an intraocular micro-display (IOMD) implant from an auxiliary head unit are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of the IOMD system disclosed herein are suitable for patients with intact retinas, yet are blind due to vascularization, occlusion, opacity, or otherwise damage of the cornea. The disclosed IOMD system seeks to restore sight to these patients by implanting an electronic micro-display (referred to as an intraocular micro-display or IOMD) into the eye, such as in the capsular sack region of the eye previously occupied by an excised lens. The IOMD is included within an IOMD implant to project reproduced images onto the patient's fully functioning retina.

Embodiments disclosed herein leverage advances in wireless power transfer technologies and miniaturized electronics to achieve wireless power transfer and wireless image data transfer from an auxiliary head unit that is worn on, or otherwise mounted to, the patients head. The power and image data signals are wirelessly communicated to an IOMD implant that is surgically positioned in the same area of the eye where an intraocular lens (IOL) would be placed. As such, the form factor of the IOMD implant should be compact, leaving little room for onboard energy storage, data processing, and data reception circuitry. Accordingly, some embodiments disclosed herein describe a batteryless implant that instead relies upon inductive charging of a compact capacitor (e.g., supercapacitor). Capacitors have much longer life spans than rechargeable batteries, thus reducing the need for surgically replacing a battery. In some embodiments, the inductive charging circuitry is used to extract a clock signal from the auxiliary head unit, which is then leveraged to support higher frequency/bandwidth synchronous data communications (e.g., for real-time image transfer) between the IOMD implant and the auxiliary head unit. With synchronous data communications and inductive charging, fewer, simpler, and more compact electronic components with longer serviceable lifespans are used within the IOMD implant to support high bandwidth wireless data communications between the auxiliary head unit and the IOMD implant.

An IOMD that runs at a traditional full color, 20 fps may consume significant power, and thus generate significant heat, over sustained periods of operation. Accordingly, some embodiments describe the use of an acknowledgement (ACK) signaling protocol from the IOMD implant back to the auxiliary head unit to throttle power consumption based upon implant temperature, power reception strength, and overall power budgeting needs of the system. In various embodiments, power consumption is throttled by adjusting image frame rates and/or by fading multi-color images to monochromatic images using a variety of techniques as described below.

Figure 1B:
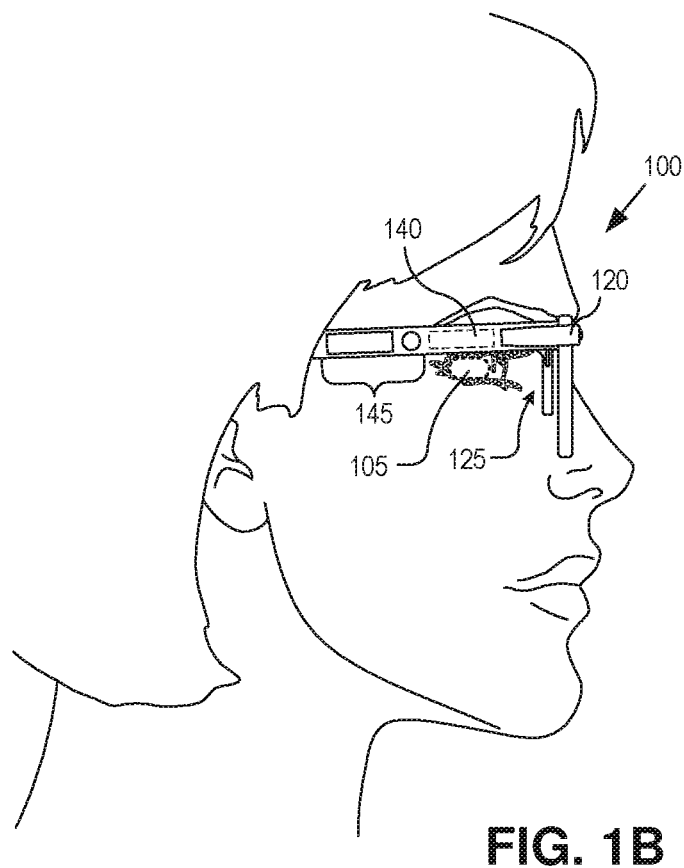
Figure 1C:
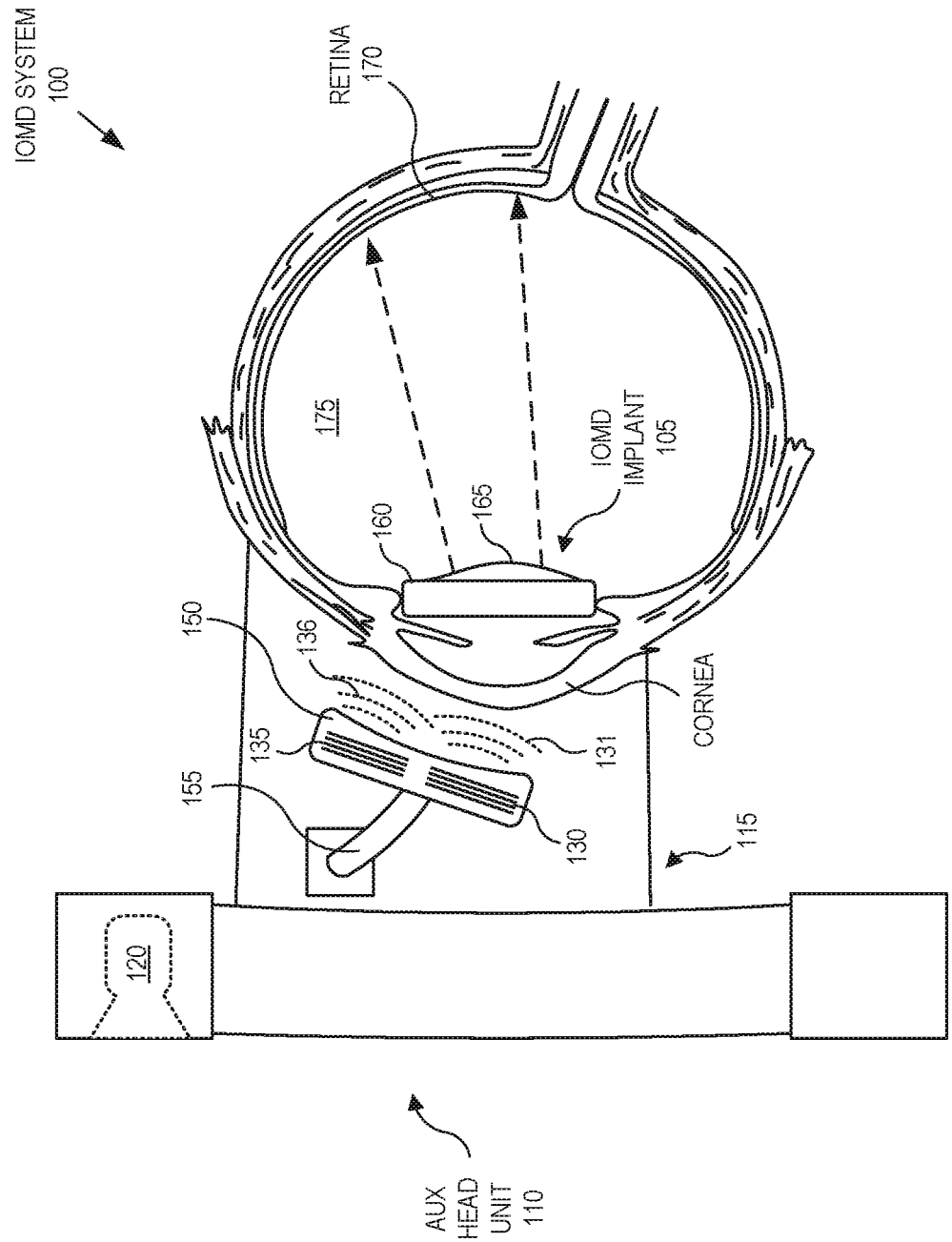
FIG. 1C is a cross-sectional illustration of the IOMD system with the the IOMD implant implanted within an eye for projecting images onto a retina, in accordance with an embodiment of the disclosure.

FIGS. 1A, 1B, and 1C illustrate an IOMD system 100 that includes an IOMD implant 105 and an auxiliary head unit 110, in accordance with an embodiment of the disclosure. FIGS. 1A and 1B are plan and side view illustrations, respectively, while FIG. 1C is a cross-sectional illustration of IOMD system 100. The illustrated embodiment of auxiliary head unit 110 includes a frame 115, a camera module 120, an antenna mount 125, a charging antenna 130, a data antenna 135, embedded electronic circuitry 140, and a user interface 145. The illustrated embodiment of antenna mount 125 includes a flexible eye-safe enclosure 150 mounted to frame 115 via an articulating arm 155. The illustrated embodiment of IOMD implant 105 includes an enclosure 160 in which electronics are disposed along with focusing optics 165.

During operation auxiliary head unit 110 inductively powers IOMD implant 105 via power signal 131 output from charging antenna 130. Auxiliary head unit 110 further captures forward facing images with camera module 120 and wirelessly transmits those images to IOMD implant 105 via data signals 136. In one embodiment, this image capture and transmit is executed in real-time. IOMD implant 105 harvests energy from power signal 131, uses that energy to power receiver and controller circuitry for decoding data signals 136 and display circuitry for projecting the image onto retina 170 of eye 175. Again, in one embodiment, the reception, decoding, and display of the image data are executed in real-time and provide the user with virtual, real-time, forward facing vision.

Auxiliary head unit 110 includes frame 115 for mounting auxiliary head unit 110 to the user's head. Although FIGS. 1A-C illustrate frame 115 in the shape of eyeglasses, it should be appreciated that frame 115 may assume a variety of different shapes and configurations for mounting to the user's head including an eyepatch, googles, a visor, headgear, or otherwise. Camera module 120 is disposed in or on frame 120 and oriented to acquire images in the direction of the user's forward vision. Antenna mount 125 includes an articulating arm 155 to get at least power antenna 130 close to the user's eye 175 for effective wireless charging of IOMD implant 105. As such, antenna mount 125 includes a flexible eye-safe enclosure 150 in which charging antenna 130 is disposed. In the illustrated embodiment, data antenna 135 is also disposed within flexible eye-safe enclosure 150 for close proximity to IOMD implant 105. In other embodiments, data antenna 135 may be disposed elsewhere within frame 115. In yet another embodiment, power antenna 130 and data antenna 135 may be the same physical antenna operated at different frequencies. Eye-safe enclosure 150 may be fabricated of a variety of soft, flexible, dielectric materials, such as molded silicon, etc. Although FIGS. 1A-C illustrate auxiliary head unit 115 as a single contiguous frame, in other embodiments, auxiliary head unit 115 may be segmented into two or more body-wearable modular components that may be interconnected and mounted or worn in various locations about the body or clothing. Furthermore, although FIGS. 1A-C illustrate a monocular IOMD system, the illustrated components may be replicated to implement a binocular IOMD system.

As illustrated, IOMD implant 105 is entirely disposed within eye 175 and does not include electronic cables or tethers extending out of eye 175 to auxiliary head unit 110. Similarly, auxiliary head unit 110 is an independent, discrete unit that is worn on the user's head. Auxiliary head unit 110 includes embedded electronics for powering and orchestrating the operation of IOMD system 100 including itself and IOMD implant 105.

Figure 2:
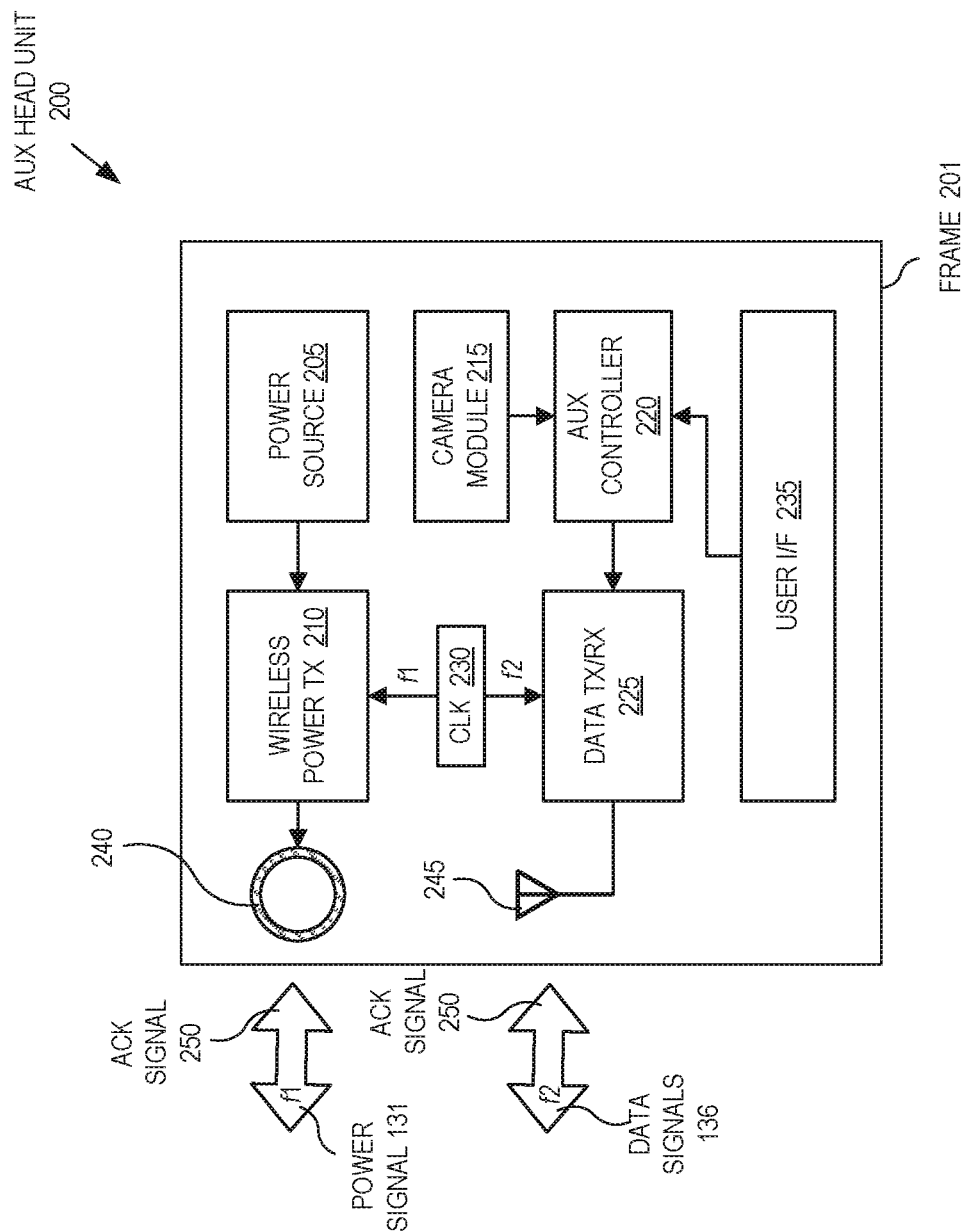
FIG. 2 is a functional block diagram of an auxiliary head unit, in accordance with an embodiment of the disclosure.

FIG. 2 is a functional block diagram of an auxiliary head unit 200, in accordance with an embodiment of the disclosure. Auxiliary head unit 200 is one possible implementation of auxiliary head unit 110. The illustrated embodiment of auxiliary head unit 200 includes a frame 201, a power source 205, a wireless power transmitter 210, a camera module 215, an auxiliary controller 220, a data transceiver 225, a clock 230, a user interface 235, a power antenna 240, and a data antenna 245.

Power source 205 is provided within frame 201 to power the internal electronics of auxiliary head unit 200 and IOMD implant 105 via inductive power transfer. In one embodiment, power source 205 is a rechargeable battery (e.g., lithium ion battery). IOMD implant 105 is inductively charged via wireless power transmitter 210 and power antenna 240. In one embodiment, wireless power transmitter 210 emits power signal 131 as a continuous wave signal having a sufficiently low frequency f1 (e.g., 13.5 MHz, 27 MHz, etc.) for efficient eye-safe power coupling. The frequency of wireless power transmitter 210 may be based upon clock 230. In one embodiment, clock 230 is a high fidelity, low power resonator, such as a quartz crystal oscillator.

Power source 205 also powers camera module 215, auxiliary controller 220, and data transceiver 225. Camera module 215 may include a charged coupled device (CCD) sensor, a complementary metal-oxide-semiconductor (CMOS) sensor, or otherwise that acquires the images relayed to IOMD implant 105. Data transceiver 225 transmits the image data representing the acquired images as data signals 136. Data signals 136 are encoded on a carrier signal having a frequency f2 (e.g., 2.4 GHz). Data transceiver 225 may use any number of encoding techniques including one or more of frequency modulation, phase modulation, amplitude modulation, and/or time multiplexing. Frequency f2 is higher than frequency f1, since it can be transmitted at lower power for safety and provides a higher bandwidth for transmission of still or video images. In one embodiment, frequency f2 is generated based upon clock 230 as well. For example, frequency f2 may be a multiplied or upscaled version of frequency f1, or frequency f1 may be a divided or downscaled version of frequency f2. In either case, clock signals based upon f1 and f2 may be phase aligned to support synchronous data communications where f2 is regenerated at IOMD implant 105 based upon f1.

Auxiliary controller 220 orchestrates the operation of the other functional components. For example, auxiliary controller 220 may receive and decode an acknowledgment (ACK) signal 250 from IOMD implant 105, and in response, adjust the image data sent to IOMD implant 105 to throttle power consumption of IOMD implant 105. ACK signal 250 may be received as a backscatter modulation of power signal 131 on power antenna 240, or received as an actively transmitted signal over data antenna 245. In either case, ACK signal 250 may operate as an acknowledgement that a given image frame has been received and displayed by the IOMD implant 105. Additionally. ACK signal 131 may also include an indication of reception strength of power signal 131 by IOMD implant 105 and/or an indication of operational temperature of IOMD implant 105. Thus, IOMD implant 105 may use a low bandwidth return channel to transmit acknowledgments along with power readings and temperature readings. The acknowledgments, power readings, and temperature readings may then be used by auxiliary controller 220 to throttle power consumption of IOMD implant 105 by adjusting the frame rate and/or color characteristics of the image data transmitted to IOMD implant 105.

By regulating the power consumption of IOMD implant 105, auxiliary controller 220 is also regulating the power consumption of auxiliary head unit 200, which is powering IOMD implant 105. Accordingly, auxiliary controller 220 may decide to throttle the power consumption of IOMD implant 105 because IOMD implant 105 is approaching an upper limit safe operating temperature of eye 175 (e.g., 39 to 40 degrees Celsius upper limit), or because IOMD implant 105 is not harvesting sufficient power from power signal 131 to operate at full capacity (e.g., flexible eye-safe enclosure 150 has not been properly aligned by the end user). Additionally, auxiliary controller 220 may throttle power consumption of IOMD implant 105 because power source 205 is running low on power, or in response to a user request to enter a power conserve mode of operation. Accordingly, the image data may be adjusted due to power scarcity in one or both of IOMD implant 105 or auxiliary head unit 200.

Auxiliary controller 220 may be implemented with hardware logic (e.g., application specific integrated circuit, field programmable gate array, etc.), implemented with software/firmware instructions stored in memory and executed by a microprocessor, or a combination of both. User interface 235 may include a variety of physical interfaces to enable the user to interact with IOMD system 100. For example, user interface 235 may include a touch pad to receive gesture commands (e.g., swipe forward, swipe back, tap, double tap, etc.), one or more buttons, dials, switches, knobs, or otherwise. In one embodiment, auxiliary controller 220 may generate visual feedback overlays on the acquired images that are transmitted to IOMD implant 105. These visual feedback overlays may include visual acknowledgments when the user interacts with user interface 235, power readings of power source 205, operational mode selections, temperature readings, a power coupling reading to aid the user in alignment of flexible eye-safe enclosure 150, or otherwise.

Figure 3:
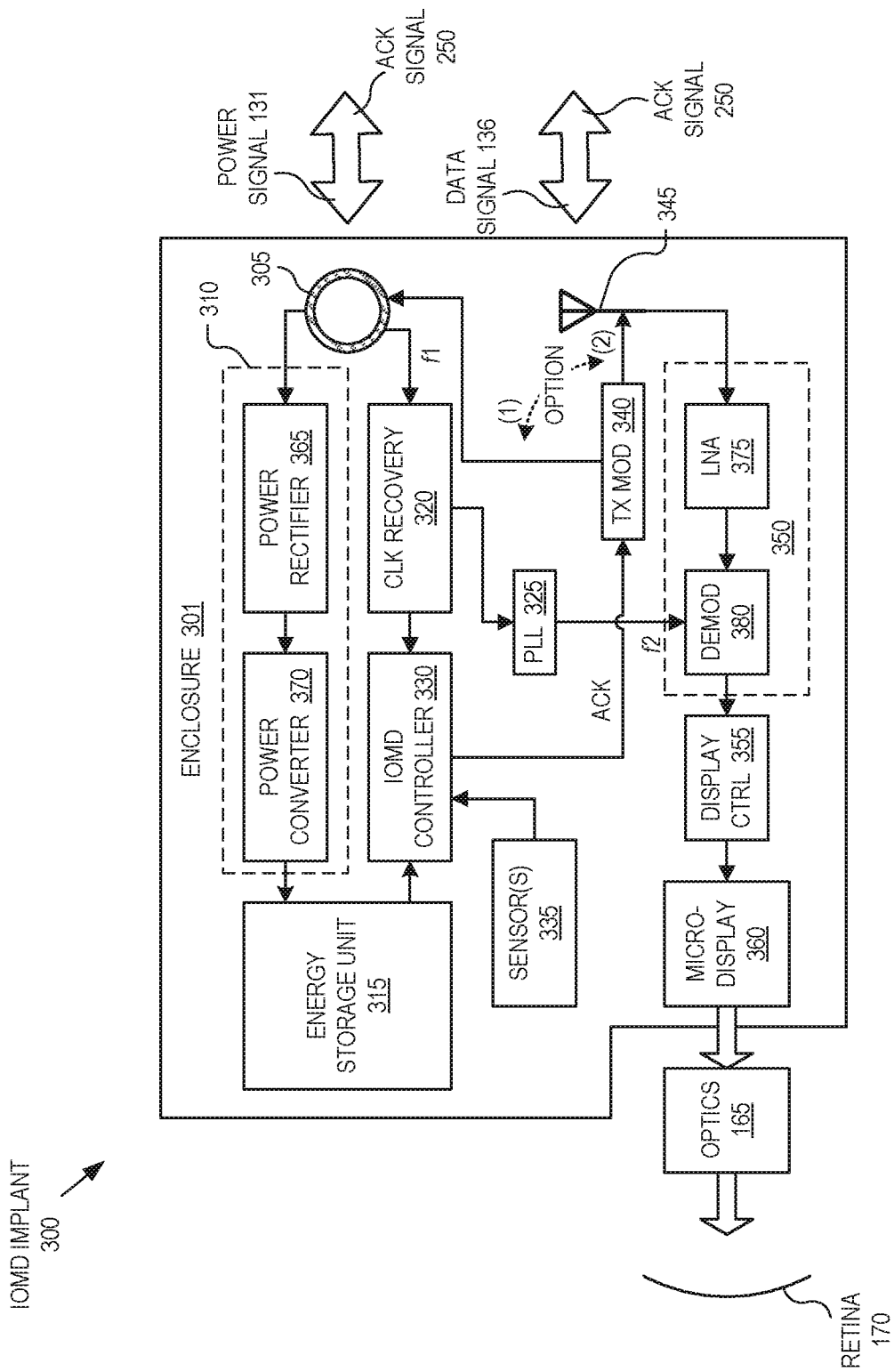
FIG. 3 is a functional block diagram of an IOMD implant, in accordance with an embodiment of the disclosure.

FIG. 3 is a functional block diagram of an IOMD implant 300, in accordance with an embodiment of the disclosure. IOMD implant 300 represents one possible implementation of IOMD implant 105. The illustrated embodiment of IOMD implant 300 includes an enclosure 301, a power antenna 305, power harvesting circuitry 310, an energy storage unit 315, clock recovery circuitry 320, a phase lock loop (PLL) 325, an IOMD controller 330, one or more sensors 335, a transmit module 340, a data antenna 345, receiver circuitry 350, a display controller 355, a micro-display 360, and optics 165. The illustrated embodiment of power harvesting circuitry 310 includes a power rectifier 365 and a power converter 370. The illustrated embodiment of receiver circuitry 350 includes a low noise amplifier (LNA) 375 and a demodulator 380.

In the illustrated embodiment, the electronic components of IOMD implant 300 are housed within a biocompatible enclosure 301 that is sized and shaped for implantation into eye 175. In one embodiment, enclosure 301 is sized for implantation into the region of the capsular sack of eye 175. In one embodiment, enclosure 301 is a hermetically sealed enclosure fabricated of metal, polymers, or otherwise.

During operation, power signal 131 output from auxiliary head unit 110 is incident upon power antenna 305. In various embodiments, power antenna 305 is disposed in or on enclosure 301. In yet other embodiments, power antenna 305 may be externally attached or tethered to enclosure 301, and implanted into another region of eye 175, such as under the sclera. In one embodiment, power antenna 305 is a loop antenna suitable for harvesting inductive power operating at frequency f1. Power harvesting circuitry 310 is coupled to power antenna 305 to harvest the wireless power incident thereon. Power harvesting circuitry 310 includes power rectifier 365 and power converter 370. In one embodiment, power rectifier 365 is implemented with one or more diodes for rectification while power converter 370 is implemented as a direct current (DC) to DC buck converter. Other power harvesting circuitry components may be used. Power harvesting circuitry 310 is used to charge energy storage unit 315. In one embodiment, energy storage unit 315 is implemented with a capacitor, such as a supercapacitor. In yet other embodiments, a rechargeable battery may be implemented, though such implementations may have a shorter life span, and thus requiring periodic surgical replacement. Alternatively, energy storage unit 315 may be implanted into another region of eye 175 (e.g., under the sclera) and tethered to enclosure 301. Placing a battery within the sclera may provide for less invasive replacement procedures. However, the components are all implanted into eye 175, and thus less susceptible to infection compared to a transcutaneous tether extending external to the eye.

Clock recovery circuitry 320 is also coupled to power antenna 305 to extract and recover a synchronous clock signal from power signal 131 from auxiliary head unit 200. Accordingly, clock recovery circuitry 320 operates to recover the lower frequency f1 from the carrier wave of power signal 131. Frequency f1 (or a partial/whole multiple thereof) is then provided to the other circuit components of IOMD implant 300 for synchronous timing. In particular, PLL 325 may be used to lock onto the phase of the synchronous clock output from clock recovery 320 and an upconverted frequency f2 provided to receiver circuitry 350 to synchronously demodulate data signal 136 received from auxiliary head unit 200 over data antenna 345. Receiver circuitry 350 includes LNA 375 to amplifier data signal 136 and demodulator 380 to down convert and decode the higher frequency f2 data signal 136. Demodulator 380 may be implemented using a variety of decoding circuits, such as, an energy detect circuit, an IQ receiver, or otherwise. Data signals 136 may be modulated using one or more of frequency modulation, phase modulation, amplitude modulation, quadrature modulation, etc.

The decoded data signals 136 are then provided to display controller 355 as the image data to be displayed by micro-display 360. In one embodiment, micro-display 360 is implemented as a multi-color light emitting diode (LED) display array. In other embodiments, micro-display 360 is a backlit liquid crystal display (LCD) or otherwise. Micro-display 360 outputs the image based upon the received image data, which is projected through focusing optics 165 onto retina 170.

IOMD implant 300 also includes IOMD controller 330, which serves to orchestrate the operation of the other functional components of IOMD implant 300. As with auxiliary controller 220, IOMD controller 330 may be implemented in hardware logic, implemented in software/firmware logic stored to a machine readable medium and executed by a microcontroller, or implemented in a combination of both.

In the illustrated embodiment, IOMD controller 330 is coupled to receive sensor readings from one or more sensors 335. Sensor(s) 335 may include a temperature sensor to monitor the operational temperature of IOMD implant 300. In this regard, the temperature sensor is a proxy reading for power consumption or power dissipation within IOMD implant 300. The temperature sensor also serves as a safety measure to ensure the eye tissue surrounding IOMD implant 300 is not damaged due to elevated operational temperatures.

In one embodiment, sensors 335 also include a voltage sensor coupled to energy storage unit 315 to measure and monitor the voltage across the electrodes of energy storage unit 315, and thus measure the stored energy. The measured voltage across energy storage unit 315 may also serve as a proxy for, or an indication of, the reception strength of power signal 131. Alternatively, sensors 335 may be coupled to power harvesting circuitry 310 and/or power antenna 305 to directly measure received voltage.

IOMD controller 330 further includes logic for generating the ACK signal, which is transmitted back to the auxiliary head unit 200 via transmit module 340 as a feedback data path. Auxiliary head unit 200 uses the ACK signal to manage overall system power consumption by adjusting frame rates, color fading, and transmit power. The ACK signal may operate as an acknowledgment of each received image frame, an indication that the data frame was correctly received and displayed, an indication of the operating temperature of IOMD implant 300, and an indication of reception strength (or a proxy thereof, such as voltage level on energy storage unit 315).

FIG. 3 illustrates two options for implementing the feedback data path. Option (1) illustrates transmit module 340 coupled to power antenna 305 to provide the feedback data path over the lower frequency f1 wireless power charging path. With option (1), transmit module 340 operates as an RFID tag to modulate the impedance of power antenna 305 and generate ACK signal 250 as a backscatter modulation of power signal 131. Option (2) illustrates transmit module 340 coupled to data antenna 345 to provide the feedback data path over the high frequency f2 wireless data signal path. With option (2), transmit module 340 is an active transmitter for generating ACK signal 250. Of course, options (1) and (2) need not be mutually exclusive, but rather, in some embodiments, both options may be implemented and used selectively based upon available power budget and bandwidth needs for the feedback data path.

In one embodiment, power antenna 305 is shaped as a loop antenna to harvest radio frequency or microwave frequency wireless power. However, it should be appreciated that power antenna 305 may assume a variety of sizes and shapes to harvest power from various frequencies of electromagnetic (EM) radiation. Similarly, data antenna 345 may assume a variety of different sizes and shapes to effectively receive (and optionally transmit) data signals 136 and/or ACK signal 250 at the higher frequency f2 (e.g., 2.4 GHz or otherwise). For example, data antenna 345 may be a dipole antenna, a patch antenna, or otherwise. In one embodiment, data antenna 345 is an optical antenna (e.g., photo receiver or photo transceiver) and data signals 136 are optical wavelength EM radiation. In yet another embodiment, power antenna 305 and data antenna 345 may be implemented as a single physical antenna that is shared between power harvesting circuitry 310, receiver circuitry 350, and transmit module 340. The sharing may be time sharing or frequency sharing where power harvesting circuitry 310 and transmit module 340 operate at frequency f1 while receiver circuitry 350 operates on frequency f2. In this shared embodiment, power antenna 305 and data antenna 345 are graphical representations of the different functional uses for a single physical antenna.

Figure 4:
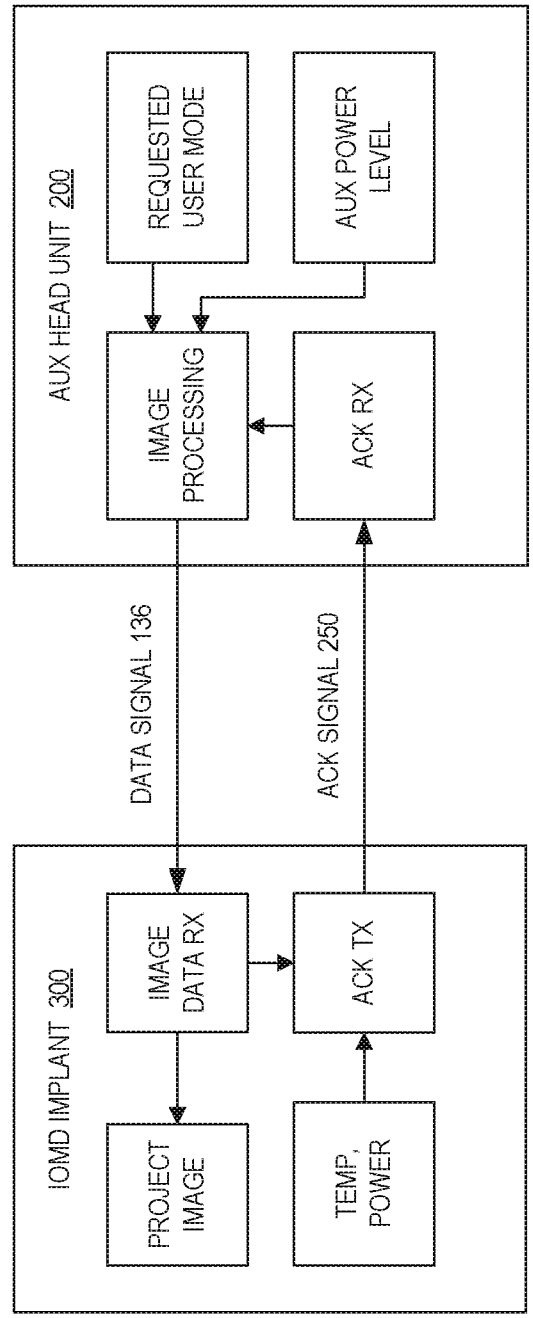
FIG. 4 is a block diagram illustrating a communication protocol between the IOMD implant and the auxiliary head unit for delivering power and image data to the IOMD implant from the auxiliary head unit, in accordance with an embodiment of the disclosure.

FIG. 4 is a block diagram illustrating a communication protocol between IOMD implant 300 and auxiliary head unit 200 for delivering power and image data to IOMD implant 300 from auxiliary head unit 200, in accordance with an embodiment of the disclosure. During operation, IOMD implant 330 receives data signal 136. Receiver circuitry 350 decodes the data signal 136 to extract the image data, which is passed to micro-display 360 for projection of an image frame onto the retina 170. In response, IOMD controller 330 commences building an ACK packet to acknowledge accurate reception and display of the image frame. Additionally, IOMD controller 330 monitors sensors 335 to determine the operating temperature of IOMD implant 300 and voltage level of energy storage unit 315. In one embodiment, the voltage level of energy storage unit 315 is deemed to be a proxy for, or indication of, the reception or coupling strength of power signal 131 at power antenna 305. IOMD controller 330 then generates the ACK packet for transmission as ACK signal 250. In one embodiment, the ACK packet includes the acknowledgment, an indication of the current operating temperature, and an indication of the reception strength of power signal 131. ACK signal 250 is then transmitted to auxiliary head unit 220.

In response to receiving ACK signal 250, auxiliary head unit 220 decodes the ACK packet to determine whether the previous image frame was received, the operating temperature of IOMD implant 300, and the received power available to IOMD implant 300. With this information, auxiliary controller 220 is able to make informed decisions for adjusting the frame rate and color fading of the image data encoded and transmitted to IOMD implant 300. By adjusting the frame rate and color fading, auxiliary controller 220 effectively throttles the power consumption of IOMD implant 300. In addition to considering the operating temperature and power reception of IOMD implant 300, auxiliary controller 220 may also consider user requests (e.g., requests received via user interface 235) and the power level of power source 205 within auxiliary head unit 200. For example, the user may request a power save mode, a high frame rate mode, etc. Accordingly, auxiliary controller 220 operates as the master of IOMD implant 300 taking into account user requests and its own power level, as well as, feedback from IOMD implant 300, when throttling the power consumption of IOMD implant 300.

Figure 5:
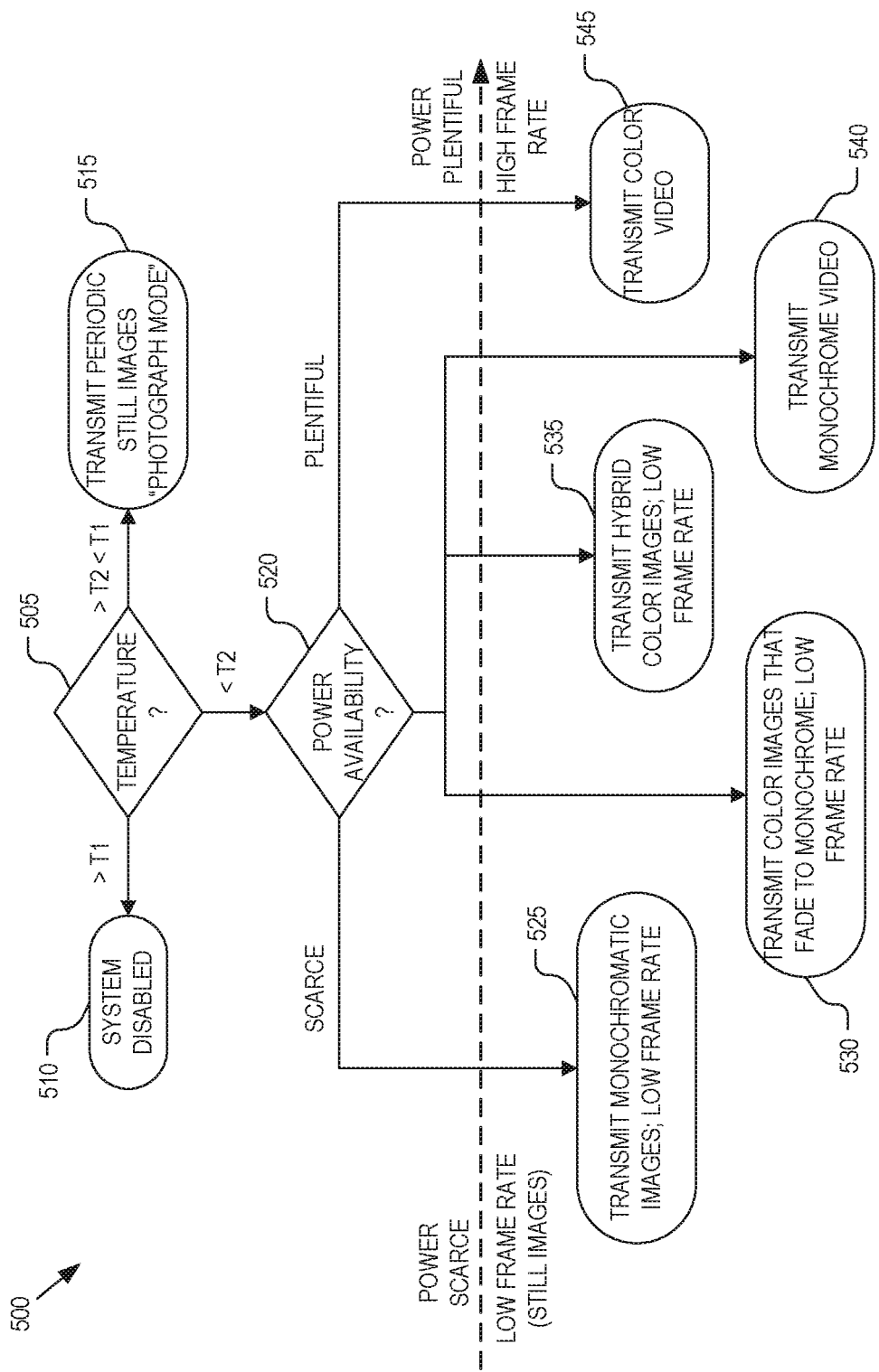
FIG. 5 is a flow chart illustrating a process for adjusting image data transmitted to the IOMD implant based upon an ACK signal to throttle power consumption of the IOMD implant, in accordance with an embodiment of the disclosure.

FIG. 5 is a flow chart illustrating a process 500 executed by auxillary controller 220 for adjusting image data transmitted to IOMD implant 300 to throttle power consumption of IOMD implant 300, in accordance with an embodiment of the disclosure. The decisions made by auxiliary controller 220 are based upon one or more of user requests, power levels (both IOMD implant received power and auxiliary head unit battery levels), and operating temperature of IOMD implant 300.

In a decision block 505, auxiliary controller 220 inspects ACK signal 250 to determine the reported operating temperature of IOMD implant 300. If the operating temperature of IOMD implant 300 is greater than a temperature threshold T1 (e.g., T1=39 degrees Celsius), then auxiliary controller 220 ceases transmission of image data to IOMD implant 300 (process block 510). For example, the upper threshold T1 may be selected to be no more than 2 degrees Celsius above the expected body temperature of a human eye so as not to impart deleterious thermal heating or stress on the surrounding eye tissue. Additionally. IOMD implant 300 may include a safety mechanism that automatically disables IOMD implant 300 should its temperature rise above temperature threshold T1 (process block 510). However, if the operating temperature of IOMD implant 300 is reported as residing between temperature thresholds T1 and T2 (e.g., T1=39 degrees Celsius and T2=37 degrees Celsius), then auxiliary controller 220 reduces the frame rate of images transmitted to IOMD implant 300 to reduce the processing power and heat dissipation needed to decode the images (process block 515). For example, the frame rate may be reduced to transmitting still images on a periodic basis (e.g. one image every 2 secs, 5 secs, 10 secs, or otherwise). This mode of operation may be referred to as "photograph mode." The images transmitted in "photograph mode" may be color images, monochromatic images, or even fading combinations of monochromatic and multi-color images, as discussed below in connection with FIG. 6. The use of monochromatic images (or partial monochromatic images) consumes less power since fewer LEDs in a micro-LED display are activated.

Figure 6:
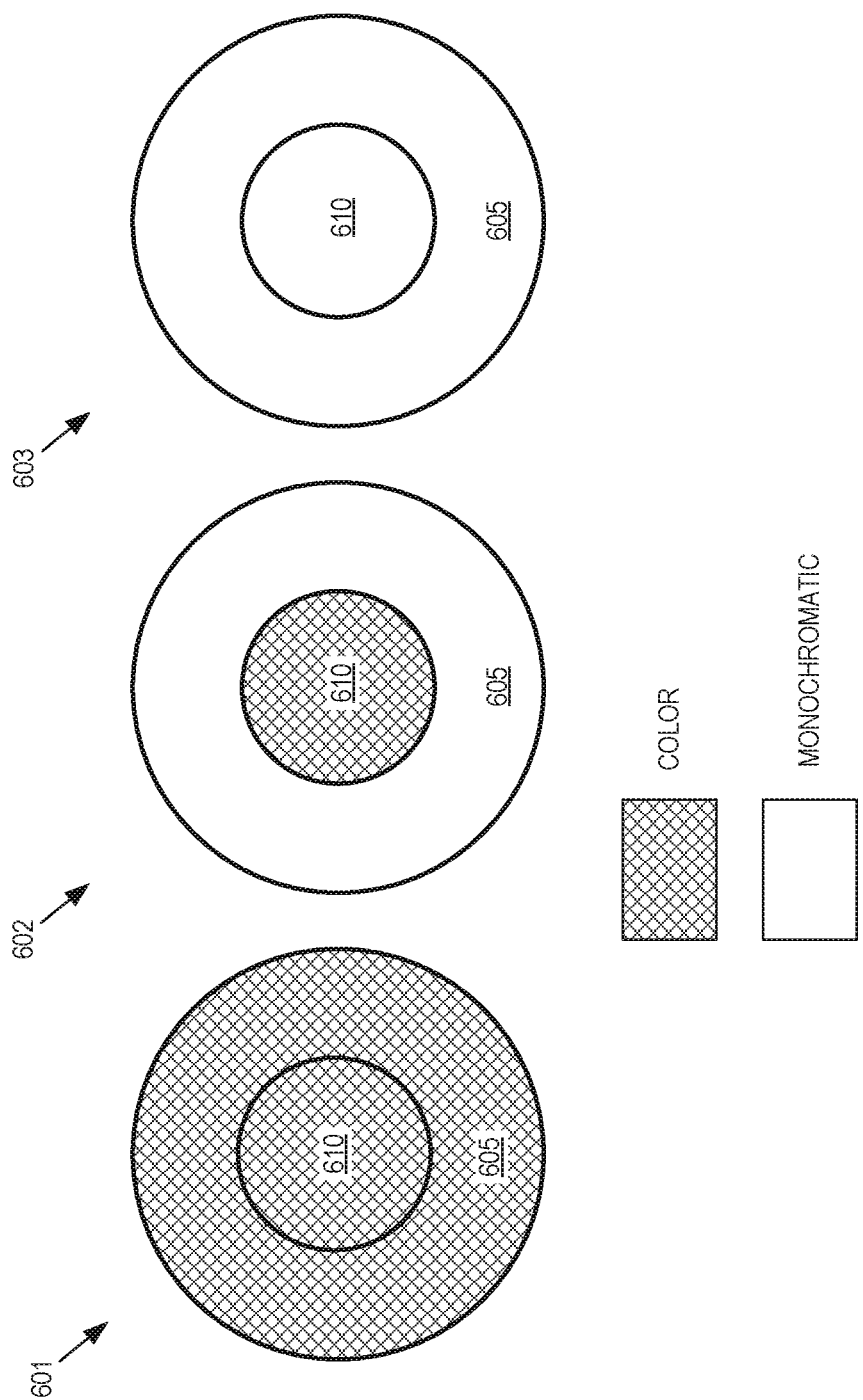
FIG. 6 is a diagram illustrating techniques of fading images transmitted to the IOMD implant between multi-color and monochrome, in accordance with an embodiment of the disclosure.

Returning to decision block 505, if the operating temperature of IOMD implant 300 is reported as being below temperature threshold T2, then process 500 continues to a decision block 520. In decision block 520, auxiliary controller 220 throttles the power consumption of IOMD implant 300 based upon the available power. Power consumption is throttled by adjusting frame rate and/or color fading of the transmitted image data. If power is deemed to be highly scarce (either due to poor wireless power coupling between auxiliary head unit 200 and IOMD implant 300, or due to a depleted power source 205 in auxiliary head unit 200), then only monochromatic images with a low periodic frame rate (e.g., one frame every 2 seconds) are transmitted (process block 525). Referring to FIG. 6, image frame 603 is a fully monochromatic image. If more power is deemed available, then auxiliary controller 220 may transmit color images that fade to monochrome at the low periodic frame rate (process block 530). Referring to FIG. 6, auxiliary controller 220 may initially transmit a full-color image frame 601 that then fades to either a fully monochrome image frame 603 or a hybrid image frame 602. Hybrid image frame 602 includes a multi-color center region 610 and a monochromatic peripheral region 605. Multi-color center region 610 corresponds to the portion of the image frame that is projected onto the user's central foveal vision where acuity is highest. Monochromatic peripheral region 605 corresponds to the portion of the image frame that is projected onto the user's peripheral vision where acuity is diminished. Hybrid image frame 602 may also be referred to as a partially monochromatic image. If yet more power is deemed available, then auxiliary controller 220 may transmit hybrid image frames 602 with increasing frame rates (process block 535). If even more power is deemed available (or the user requests higher frame rate vision), then auxiliary controller 220 may transmit monochrome video at yet a higher frame rate (e.g., 5, 10, 20 frames/sec, or otherwise) (process block 540). Finally, if power is deemed to be plentiful, then full color, full frame rate (e.g., 20 or 30 frames/sec) video may be transmitted to IOMD implant 300.

Accordingly, image quality may be adjusted by auxiliary controller 220 to regulate power consumption. The image quality can be adjusted by reducing/increasing frame rate of the image data, or the image quality may be adjusted by fading multi-color images into monochromatic images. This fading may be accomplished over time by fading between consecutively transmitted image frames (e.g., initially transmitting full-color image frame 601 then transitioning subsequently transmitted frames to either one of image frames 602 or 603). Additionally (or alternatively), fading may be accomplished within a given image frame by transmitting only hybrid image frames 602 that are multi-color in foveal region 610, but monochromatic in peripheral region 605.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:
1. An intraocular micro-display system, comprising:
 an intraocular micro-display (IOMD) implant including:
  an enclosure shaped for implantation into an eye;
  a micro-display disposed in the enclosure and oriented to emit an image towards a retina of the eye when the IOMD implant is implanted into the eye;

an energy storage unit disposed within the enclosure and coupled to the micro-display to power the micro-display;

a first charging antenna coupled to the energy storage unit for wireless charging of the energy storage unit via a power signal incident upon the first charging antenna;

a first data antenna coupled to the micro-display to wirelessly receive image data for driving the micro-display to emit the image; and an IOMD controller with logic that when executed by the IOMD controller causes the IOMD implant to perform operations comprising:

generating an acknowledgement (ACK) signal in response to receiving an image frame, the ACK signal including an indication of reception strength of the power signal incident upon the first charging antenna; and wirelessly transmitting the ACK signal, wherein the first charging antenna and the first data antenna are implantable into the eye with the IOMD implant.

2. The intraocular micro-display system of claim 1, wherein the first charging antenna and the first data antenna are disposed in or on the enclosure of the IOMD implant.

3. The intraocular micro-display system of claim 1, wherein the IOMD implant further includes:

a temperature sensor coupled to the IOMD controller and configured to measure a temperature of the IOMD implant, wherein generating the ACK signal includes generating the ACK signal with an indication of the temperature of the IOMD implant.

4. The intraocular micro-display system of claim 3, further comprising an auxiliary head unit, the auxiliary head unit including:

a camera module to capture the image;

a second charging antenna to emit the power signal towards the IOMD implant when the auxiliary head unit is worn on the head;

a second data antenna to emit the image data towards the IOMD implant; and an auxiliary controller including logic that when executed by the auxiliary controller causes the auxiliary head unit to perform operations comprising:

adjusting the image data sent to the IOMD implant based upon the ACK signal received from the IOMD implant to throttle power consumption of the IOMD implant.

5. The intraocular micro-display system of claim 4, wherein adjusting the image data sent to the IOMD implant based upon the ACK signal comprises:

reducing a frame rate of images transmitted to the IOMD implant when power in the IOMD implant or the auxiliary head unit is determined to be scarce; and increasing the frame rate of the images transmitted to the IOMD implant when the power in the IOMD implant or the auxiliary head unit is determined to be plentiful.

6. The intraocular micro-display system of claim 4, wherein adjusting the image data sent to the IOMD implant based upon the ACK signal comprises:

reducing a frame rate of images transmitted to the IOMD implant when the temperature of the IOMD implant exceeds a threshold value; and increasing the frame rate of the images transmitted to the IOMD implant when the temperature of the IOMD implant is below the threshold value.

7. The intraocular micro-display system of claim 4, wherein adjusting the image data sent to the IOMD implant based upon the ACK signal comprises:

fading images transmitted to the IOMD implant from multi-color to monochrome.

8. The intraocular micro-display system of claim 7, wherein fading images transmitted to the IOMD implant comprises:

transmitting the images with a multi-color foveal region that transitions to a monochrome peripheral region.

9. The intraocular micro-display system of claim 4, wherein the second charging antenna is disposed within a flexible eye-safe enclosure that mounts to a frame of the auxiliary head unit via an articulating arm.

10. The intraocular micro-display system of claim 1, further comprising:

a transmit module coupled to the first charging antenna to transmit the ACK signal via the first charging antenna as a backscatter modulation of the power signal.

11. The intraocular micro-display system of claim 1, wherein the IOMD implant further comprises:

a clock recovery unit coupled to the first charging antenna to recover a clock signal from the power signal; and a demodulator coupled to the clock recovery unit and having synchronous timing based upon the clock signal recovered from the power signal to provide synchronous data reception of the image data via the first data antenna, wherein the image data is received on a carrier wave having a higher frequency than that of the power signal.

12. The intraocular micro-display system of claim 1, wherein the energy storage unit comprises a capacitor.

13. The intraocular micro-display system of claim 1, wherein the first charging antenna and first data antenna comprise physically distinct antennas.

14. An intraocular micro-display (IOMD) implant comprising:

an enclosure shaped for implantation into an eye;

a micro-display disposed in the enclosure and oriented to emit an image towards a retina of the eye when the IOMD implant is implanted into the eye;

an energy storage unit disposed within the enclosure and coupled to the micro-display to power the micro-display;

a first charging antenna coupled to the energy storage unit for wireless charging of the energy storage unit via a power signal incident upon the first charging antenna;

a first data antenna coupled to the micro-display to wirelessly receive image data for driving the micro-display to emit the image; and an IOMD controller with logic that when executed by the IOMD controller causes the IOMD implant to perform operations comprising:

generating an acknowledgement (ACK) signal in response to receiving an image frame, the ACK signal including an indication of reception strength of the power signal incident upon the first charging antenna; and wirelessly transmitting the ACK signal, wherein the first charging antenna and the first data antenna are implantable into the eye with the IOMD implant.

15. The IOMD implant of claim 14, wherein the first charging antenna and the first data antenna are disposed in or on the enclosure of the IOMD implant.

16. The IOMD implant of claim 14, further comprising: a temperature sensor coupled to the IOMD controller and configured to measure a temperature of the IOMD implant,
   wherein generating the ACK signal includes generating the ACK signal with an indication of the temperature of the IOMD implant.

17. The IOMD implant of claim 14, further comprising a transmit module coupled to the first charging antenna to transmit the ACK signal via the first charging antenna as a backscatter modulation of the power signal.

18. The IOMD implant of claim 14, further comprising:
   a clock recovery unit coupled to the first charging antenna to recover a clock signal form the power signal; and
   a demodulator coupled to the clock recovery unit and having synchronous timing based upon the clock signal recovered from the power signal to provide synchronous data reception of the image data via the first data antenna, wherein the image data is received on a carrier wave having a higher frequency than that of the power signal.

19. The IOMD implant of claim 14, wherein the energy storage unit comprises a capacitor.

20. The IOMD implant of claim 14, wherein the first charging antenna and the first data antenna comprise physically distinct antennas.

* * * * *